United States Patent [19]

Trau et al.

[11] Patent Number: 5,023,081
[45] Date of Patent: Jun. 11, 1991

[54] CONTROLLED RELEASE HYDROXYBUTYRATE POLYMER MICROSPHERES

[75] Inventors: Matt Trau, Northcote; Rowan W. Truss, Oak Park, both of Australia

[73] Assignee: ICI Australia Operations Proprietary Limited, Melbourne, Australia

[21] Appl. No.: 328,156

[22] PCT Filed: May 24, 1988

[86] PCT No.: PCT/AU88/00157
§ 371 Date: Jan. 27, 1989
§ 102(e) Date: Jan. 27, 1989

[87] PCT Pub. No.: WO88/09121
PCT Pub. Date: Dec. 1, 1988

[30] Foreign Application Priority Data
May 29, 1987 [AU] Australia ............................... PI2220

[51] Int. Cl.$^5$ ................................................. A61K 9/50
[52] U.S. Cl. .................................... 424/405; 424/408; 424/409; 424/417; 424/490; 424/497
[58] Field of Search ............... 424/408, 409, 486, 419, 424/405, 417, 407, 490, 497

[56] References Cited

U.S. PATENT DOCUMENTS

| | | | |
|---|---|---|---|
| 4,148,871 | 4/1979 | Pitt et al. | 424/426 X |
| 4,181,983 | 1/1980 | Kulkarni | 424/426 X |
| 4,291,013 | 9/1981 | Wahlig et al. | 424/426 |
| 4,328,204 | 5/1982 | Wasserman et al. | 424/426 X |
| 4,347,234 | 8/1982 | Wahlig et al. | 424/426 |
| 4,419,340 | 12/1983 | Yolles | 424/486 X |
| 4,491,575 | 1/1985 | Korsatko | 424/426 X |
| 4,675,189 | 6/1987 | Kent et al. | 424/426 X |

*Primary Examiner*—Thurman Page
*Assistant Examiner*—James Spear
*Attorney, Agent, or Firm*—Cushman, Darby & Cushman

[57] ABSTRACT

Controlled release microspheres of hydroxybutyrate polymer comprise active ingredient and hydroxybutyrate/hydrovalerate copolymer. The microspheres comprise a skin which is distinct from the general bulk of the microspheres, and this skin may have a porosity covering from 0–50% of the total surface area of the microsphere, this porosity being largely controlled by varying the hydroxyvalerate content of the polymer. The porosity of the interior of the microspheres can also be regulated. Control of the two porosities permits the attainment of a wide range of release rates for a wide range of active ingredients. The microspheres can be used in a wide variety of pharmaceutical, veterinary and agricultural applications.

10 Claims, No Drawings

CONTROLLED RELEASE HYDROXYBUTYRATE POLYMER MICROSPHERES

This invention relates to the microencapsulation of active substances and to microspheres thus prepared.

The microencapsulation of active substances, that is, substances which have a chemical or biological effect in a suitable environment, is a technique which is well known to the art. Typical examples of active substances which have been encapsulated are drugs and fungicides. The possible reasons for microencapsulation are numerous, for example, to permit the administration of an active substance which could not otherwise be administered, to preserve the active substance in a hostile environment until it can be released in the correct environment, or to extend the release of an active substance over a period of time so as to extend correspondingly the effect of the active substance. The two last-named categories are often described as "controlled release" applications. Controlled release is an especially useful property in fields such as pharmaceuticals where use has been made of gelatin capsules. A more recent development is the use of microspheres, especially those prepared by solvent evaporation. In this case, the active substance and the microsphere- forming material are dissolved or dispersed in a liquid, commonly an organic liquid, which is then dispersed in a liquid in which the organic liquid is immiscible (water is commonly used) and the organic liquid removed by evaporation to leave microspheres.

The procedure is described by Bissery and co-workers in a paper given at the 3rd Exposition-Congress of the International Technology of Pharmacy (Assoc. Pharm. Galénique Ind. 1983), Vol. 3, pp. 233–9. This paper describes the application of the technique to a number of polymers, including poly($\beta$-hydroxybutyrate). This polymer is described in a further publication by Bissery (chapter 4 of "Microspheres and Drug Therapy : Pharmaceutical, Immunological and Medical Aspects", ed. Davis, Illum, McVie and Tomlinson, Elsevier 1984, pp 217-227) in connection with the anticancer agent CCNU.

Bissery has observed that the surface of a poly($\beta$-hydroxybutyrate) (hereinafter referred to as "PHB"; microsphere contains many macroscopic surface pores. This undoubtedly contributes to the fact that PHB microspheres release the active substances encapsulated therein very quickly; the release rates given by Bissery in the second publication referred to hereinabove are very high. However, this speed of release is not suitable for the whole range of active substances and this limits the usefulness of PHB.

It has now been found that it is possible to prepare microspheres comprising PHB wherein the release rate may be altered in a predictable manner. There is therefore provided, according to the present invention, controlled release hydroxybutyrate polymer microspheres comprising at least one active substance, the polymer comprising a copolymer of 3-hydroxybutyric acid and 3-hydroxyvaleric acid, and the microspheres comprising a continuous skin covering the surface thereof.

PHB, sometimes known in the literature as poly(3-hydroxybutyric acid), is a thermoplastic polymer which is accumulated by many organisms. European Patent Specifications 15669 and 46344 describe typical processes for making PHB. The production of hydroxybutyrate/hydroxyvalerate copolymers is described by, for example, Wallen and co-workers in "Environmental Science and Technology" 8 (1974), 576–9.

It is a special feature of the microspheres of this invention that, in contrast to the microspheres of the known art, they have a skin, that is, a thin surface layer different in structure to that of the bulk of the microspheres. This skin is continuous over essentially the entire surface of the microspheres. It is, however, permissible that it may have pores therein which give rise to openings at the surface of the skin. The skin can in fact vary between essentially completely pore-less and quite highly porous (pore ends covering up to about 50% of the total skin surface area). It is the combination of the nature of the skin and that of the interior of the microsphere and the susceptibility of these to controllable alteration which give the microspheres of the present invention unique advantages over the known art.

The controlled release characteristics of the microspheres according to the present invention can be modified either by controlling the nature of the skin or by controlling the nature of the interior of the microspheres. The nature of the skin may be altered by varying the hydroxyvalerate content of the polymer. This can be done either by varying the hydroxyvalerate content of the copolymer itself or by blending with the copolymer a proportion of PHB homopolymer. It has been observed that as the valerate content rises, the porosity of the skin decreases. At high valerate contents, there is no skin porosity at all, and active ingredients can escape only by diffusion through the polymer matrix.

Other factors such as temperature of evaporation of the solvent, type of solvent and polymer concentration in the organic phase have some effect on skin porosity and thickness, but they exert an effect which is relatively minor in comparison to that produced by hydroxyvalerate content variation.

The interior of the microspheres may be modified in a number of ways, but they all have the common factor of varying the internal porosity of the microspheres. One way of doing this is to add amphipathic material to the copolymer. It has been observed that microspheres produced from the pure copolymer are solid, essentially non-porous spheres. However, the addition of amphipathic material, that is, material having affinity for both phases of a two phase oil/water system, increases the porosity. The amphipathic material may be, for example, a commercial surfactant or a number of such surfactants. Copolymer from some sources has been found to contain already an amphipathic natural material the nature of which is presently unknown but which can be utilised in place of an addition of amphipathic material. Thus, in order to reduce the porosity in copolymers of this type, the copolymers are purified to the required degree.

A further method of modifying the interior is by using a double emulsion technique. This is a well-known technique which involves the stable emulsification of a first liquid in a second liquid with which the first liquid is not compatible, followed by the stable emulsification of the resulting emulsion in a third liquid with which the second liquid is not compatible. Commonly, the first and third liquids are aqueous and the second liquid is a polymer or polymer precursor, such that the end result is a dispersion of polymer microspheres which comprise an inner structure, this generally comprising discrete cells or continuous porosity, depending on the nature of the polymer. In the present invention, the emulsification of an aqueous liquid into a solution of copolymer in a suitable solvent can readily give a desired degree of porosity. The internal aqueous phase may be stabilised by any of the means known to the art, for example, surfactants. It is a feature of some copolymers containing amphipathic natural material of the type described hereinabove that stabilisation of the internal aqueous phase is achieved by this means alone, without further addition of surfactant.

The active substance for use in this invention can be any suitable active substance. It can be, for example, a pharmaceutical, a herbicide, an insecticide or a fungicide. Because of the ability (hereinabove described) to alter the surface morphology and therefore the release characteristics of the microspheres according to this invention, an unusually wide range of active substances can be accommodated. It is of course permissible to incorporate more than one active substance in a single microsphere. The active ingredient may be incorporated directly into the copolymer, or in solution or dispersion form. It may be within the cells or pores, the polymer matrix or both.

The microspheres of this invention may be prepared by any means known to the art suitable for the preparation of such microspheres of suitable skin and internal structure. For example, they may be prepared by the solvent evaporation method described in the Bissery publications referred to hereinabove. An alternative method is the double emulsion method hereinabove described. A third method is that described in a copending Australian patent applicant by the same applicant, wherein a copolymer solution is added to a continuous phase which contains the active ingredient.

The invention is further illustrated by the following examples in which all parts are expressed by weight.

EXAMPLE 1

Preparation of microspheres containing a pesticide 1 part of a hydroxybutyrate/hydroxy- valerate copolymer (19% valerate content by weight) and 0.25 parts of "Chlorpyrifos" (trade mark) pesticide were dissolved in 30 parts chloroform. This mixture was added to a stirred, heated (55° C.) aqueous solution (0.27%) of an 82% hydrolysed grade of polyvinyl acetate a 4% aqueous solution of which had a viscosity of 9.0 cps at 20° C. The emulsion thus formed was stirred at 250 rpm and maintained at 55° C. for 3 hours until the chloroform had completely evaporated. Washing, filtering and drying gave white microspheres of diameter of from 100–500 um.

Examination by scanning electron microscope at magnification × 700 revealed an essentially pore-free skin and sectioned microspheres exhibited a highly porous interior (approximately 40% by volume of spherical pores, the mean pore diameter being about 15 um). X-ray fluorescence revealed the presence of the pesticide within the polymer matrix.

EXAMPLE 2

An example which demonstrates the effect of raising the hydroxyvalerate content of the copolymer Example 1 was repeated, with the substitution of an identical quantity of a copolymer containing 27% hydroxyvalerate by weight. The interior of the microspheres prepared from this copolymer comprised about 70% by volume of pores with a mean pore size of about 5 um. The skin on the microspheres was essentially pore-free.

EXAMPLE 3

An example which demonstrates the effect of the removal of naturally-occurring amphipathic material Example 1 was repeated, with the additional step that the copolymer was purified prior to microsphere manufacture by twice precipitating it from chloroform solution with methanol.

The resultant microspheres were smooth-skinned (no pores) and had a porosity of 15%, the pores being spherical and of mean size 2 um. The claims defining the invention are as follows.

We claim:

1. Controlled release hydroxybutyrate polymer microspheres comprising an amphipathic material and at least one active substance selected from pharmaceuticals, herbicides, pesticides, fungicides, and mixtures thereof, the hydroxybutyrate polymer comprising a co-polymer of 3-hydroxybutyric acid and 3-hydroxyvaleric acid, and the microspheres comprising a continuous skin covering the surface thereof wherein the skin comprises pores whose total surface area expressed as a percentage of the total surface area of the microspheres is up to 50% maximum.

2. A process of administering an active ingredient at a desired locus by means of controlled release hydroxybutyrate polymer microspheres according to claim 1.

3. Controlled release hydroxybutyrate polymer microspheres according to claim 1, wherein the interior of the microspheres beneath the skin comprises porosity.

4. A process of preparing controlled release hydroxybutyrate polymer microspheres according to claim 1, wherein the surface porosity is selected by the selection of the proportion of hydroxyvalerate content of the hydroxybutyrate polymer.

5. A process according to claim 4, wherein the proportion of hydroxyvalerate in the hydroxybutyrate polymer is altered by altering the proportion thereof in the hydroxyvalerate/hydroxybutyrate copolymer.

6. A process according to claim 4, wherein the proportion of hydroxyvalerate in the hydroxybutyrate polymer is altered by the addition thereto of PHB homopolymer.

7. A process of preparing controlled release claim 3, wherein the porosity of the interior of the microspheres is determined by the inclusion in the polymer of amphipathic material.

8. A process according to claim 7, wherein the amphipathic material comprises at least one surfactant.

9. A process according to claim 7, wherein the porosity is determined by controlling the level of naturally-occurring amphipathic material in the polymer.

10. A process of preparing controlled release hydroxybutyrate polymer microspheres according to claim 3, wherein the porosity of the interior of the microspheres is determined by the use of a double emulsion process.

* * * * *